United States Patent

Cash, Jr. et al.

[11] 4,198,988
[45] Apr. 22, 1980

[54] PULSE TRANSDUCER WITH ARTIFACT SIGNAL ATTENUATOR

[76] Inventors: Alan M. Lovelace, Administrator of the National Aeronautics and Space Administration, with respect to an invention of Wilbur H. Cash, Jr., Littleton, Colo.; John T. Polhemus, Englewood, Colo.

[21] Appl. No.: 928,137

[22] Filed: Jul. 26, 1978

[51] Int. Cl.² .................................................. A61B 5/02
[52] U.S. Cl. .................................... 128/666; 128/690
[58] Field of Search ............................ 128/665–667, 128/687, 689, 690; 330/126

[56] References Cited

U.S. PATENT DOCUMENTS

| | | | |
|---|---|---|---|
| 3,296,463 | 1/1967 | Brault | 330/126 X |
| 3,572,324 | 3/1971 | Petersen | 128/706 |
| 3,769,974 | 11/1973 | Smart et al. | 128/666 |
| 3,858,574 | 1/1975 | Page | 128/689 X |
| 3,908,636 | 9/1975 | Page | 128/666 |
| 3,993,047 | 11/1976 | Peek | 128/666 |

Primary Examiner—Kyle L. Howell
Attorney, Agent, or Firm—Monte F. Mott; John R. Manning; Paul F. McCaul

[57] ABSTRACT

In combination with a pulse transducer characterized by a source of light and a detector for light reflected from blood vessels of a living body, to provide heart signal consisting of a modulated dc signal voltage indicative of the pulse rate for the body, an artifact signal resulting from a reflection of light from the skin of the body, which includes both a constant dc signal component and a modulated dc signal component the amplitude of which is greater and the frequency of which is less than said heart signal, a signal attenuator circuit including an operational amplifier for canceling said artifact signal from the output signal of the pulse transducer.

1 Claim, 1 Drawing Figure

PULSE TRANSDUCER WITH ARTIFACT SIGNAL ATTENUATOR

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The invention generally relates to attenuator circuits for reducing background noise signals, and more particularly to an artifact signal attenuator circuit for a heart-rate sensor of the type most specifically defined and claimed in U.S. Pat. No. 3,769,974 which issued Nov. 6, 1973.

2. Description of the Prior Art:

As disclosed in the aforementioned United States Letters Patent, a pulse transducer contained in a package of a wristwatch-size including a plurality of light emitting diodes which serve as a source of light may be employed to provide an output signal which varies as a function of the pulse rate of a living body. The emitted light is transmitted through the skin of the body to blood vessels from which it is reflected to a sensor with an intensity varying as a function of variations in the pulse wave pressure of the artery. Unfortunately, it has been found that light also is reflected from the skin of the body. This light also is detected by the sensor, whereupon a dc signal, hereinafter referred to as an artifact signal, appears at the output of the transducer.

In practice, the artifact signal consists of two parts; namely, a constant level dc signal, resulting from a constant reflection from the skin, and, a sinewave signal varying as reflection is varied in response to motion imparted to the sensor. The constant signal component achieves a dc level typically one hundred to two hundred times greater than the amplitude of the heart signal present at the sensor's output. When the sensor is moving with respect to the skin, a sinewave component appears around the dc level of the aforementioned artifact signal component. As should be apparent, the components of the artifact signal must be removed if the relatively small heart signal, typically ten to twenty millivolts, is to undergo high amplification.

In the presence of one-to-two volt signal components for the artifact signal the gain required to increase the amplitude of a ten-to-twenty millivolt heart signal to a useable level tends to saturate available amplifiers. The most straight-forward way to eliminate the components of the artifact signal would be to effect an ac-couple of the sensor output to filter/amplifier circuits. Unfortunately, for the signal spectrum of interest, 0.5 Hz to 4 Hz, the coupling capacitor simply is too large to meet the packaging requirements necessary to provide the electronics in a wristwatch-size package.

It is, therefore, the general purpose of the instant invention to provide a suitable attenuator circuit adapted to be connected with the output of a pulse transducer and the input of subsequent signal processing circuits, mounted in a package of wristwatch-size, for purposes of reducing the amplitude of components of an artifact signal at the sensor's output so that the heart signal provided thereby can be filtered and amplified by the further signal processing circuits.

OBJECTS AND SUMMARY OF THE INVENTION

It is an object of the instant invention to provide an artifact signal attenuator circuit for reducing the amplitude of noise signals with respect to the amplitude of desired signals simultaneously provided at a common output.

Another object is to provide in combination with a pulse transducer of a wristwatch-size having its output terminal connected to an input terminal for a further signal processing circuit and adapted to provide a sensor output signal comprising a heart signal consisting of a modulated dc signal indicative of the pulse rate for a living body, an artifact signal component comprising a constant dc signal, and a modulated dc signal having an amplitude greater and frequencies less than a heart signal, a signal attenuator circuit, suitably configured to be received in a wristwatch-size package, for substantially eliminating artifact signal components at the input terminal for a further signal processing circuit.

Another object is to provide a signal attenuator circuit particularly suited for use with a pulse transducer of a size and configuration adapted to be worn as a wristwatch-size package, although not necessarily restricted in use thereto since the circuit may be useful when employed in other systems wherein a background noise signal is slowly varying with respect to a desired signal, including ultrasound measuring systems, strain gauge measuring systems, accelerometer systems and the like.

These and other objects and advantages are achieved through the use of an operational amplifier connected around an input resistor interposed between an output terminal for the pulse transducer and an input for a further signal processing circuit, for thus applying to the input terminal a canceling signal whereby noise signal components are canceled as will hereinafter become more readily apparent by reference to the following description and claims in light of the accompanying drawings.

DESCRIPTION OF THE PREFERRED EMBODIMENT

Figure 1:
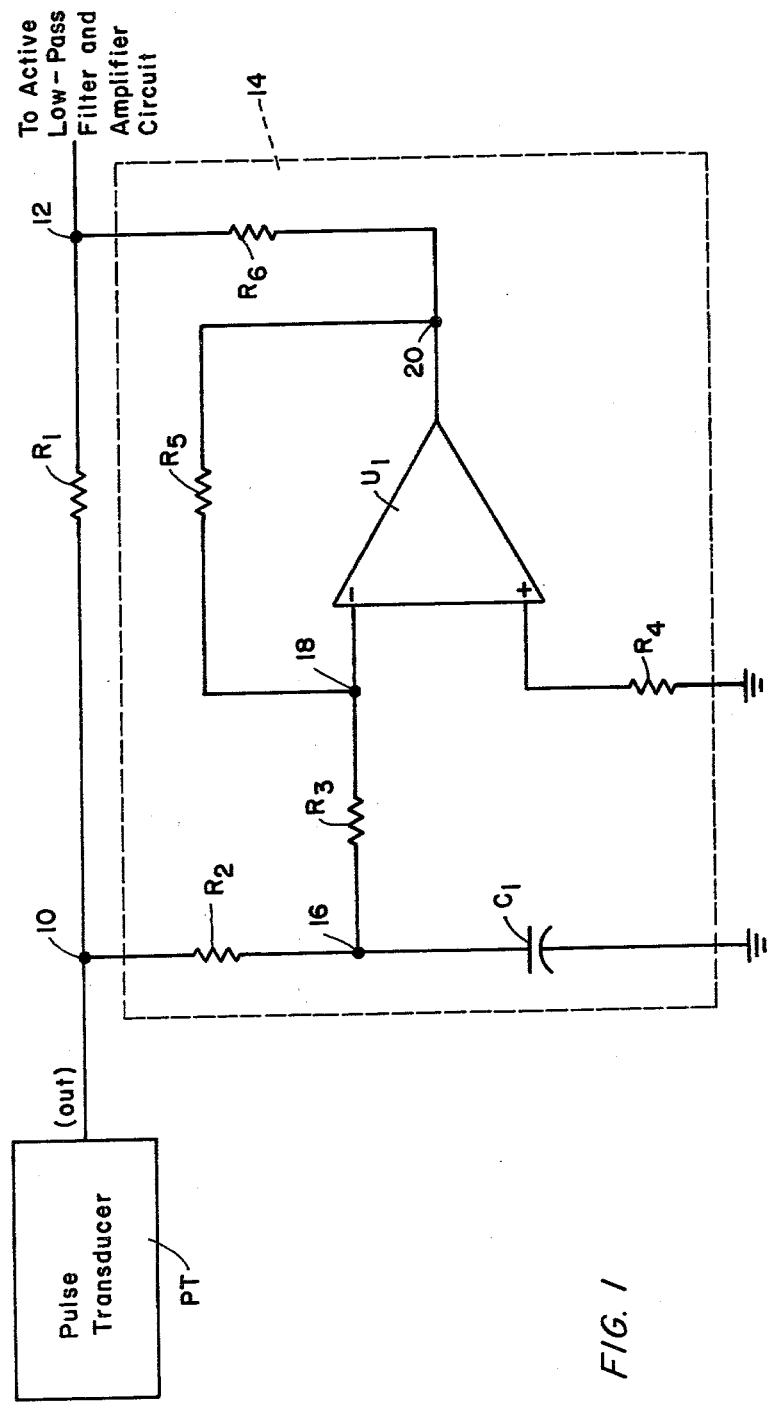
FIG. 1 is a schematic view of an attenuator circuit which embodies the principles of the instant invention.

Referring now to the drawings wherein like reference characters designate like or corresponding parts throughout the several views, there is shown in FIG. 1 a schematic view, in block diagram form, of a background noise attenuator circuit embodying the principles of the instant invention.

As shown, the attenuator circuit is coupled to an output terminal 10 for a pulse transducer PT of a type described and claimed in U.S. Pat. No. 3,769,974. Moreover, it is important to understand that the artifact attenuator circuit herein described comprises one of a plurality of signal processing circuits which may, where desired, comprise circuits of similar design. The transducer PT provides an output consisting of a heart signal comprising a modulated dc signal indicative of the pulse rate for a living body and an artifact signal comprising a constant dc signal component and modulated dc signal components having an amplitude greater and a frequency less than the heart signal. As aforementioned, the heart signal results from a reflection of light from blood vessels, while a reflection of light from the skin of the body results in an artifact signal. At this juncture, it is important to appreciate that the heart signal is within a range of 0.5 to 4 Hz, the constant dc signal component, which results from a constant reflection from the skin is at a constant level, typically one hundred to two hundred times greater than the amplitude of the heart signal, and the artifact signal component resulting from the sensor's motion comprises a sinewave appearing around the level of the constant dc component.

The output terminal 10 is connected through a 100 K (kilo-ohm) resistor $R_1$ to an input terminal 12 of an active low pass filter and amplifier circuit, not herein described. For the sake of convenience, the terminal 12 is herein described as an input terminal for a further signal processing circuit. Connected around, or in bypass relation with the resistor $R_1$ is an attenuator circuit, herein designated 14. The purpose of this circuit is to apply to terminal 12 an algebraic negative of the artifact signal appearing at terminal 10 for purposes of canceling the artifact signal from the output of the pulse transducer PT. In practice, the heart signal also undergoes attenuation but to an extent which can be tolerated.

The attenuator circuit 14 includes an operational amplifier $U_1$ having its input connected to the terminal 10. Since operational amplifiers are well known, a detailed description of the amplifier $U_1$ is omitted in the interest of brevity. However, the circuit 14 as currently configured is provided with one-fourth of an LM 324 amplifier. Interposed between the amplifier $U_1$ and the terminal 10 there is a terminal 16 to which the output terminal 10 of the pulse transducer is connected through a 100 K resistor $R_2$. A 100 K resistor $R_3$ also is connected between the terminal 16 and the input of the operational amplifier $U_1$. It should be noted that to the terminal 16 there is connected a 1 UF (microfarad) capacitor $C_1$ which cooperates with the resistor $R_2$ and serves to integrate the slowly-varying artifact signal appearing at terminal 10.

The amplifier $U_1$ also is connected through a 68 K resistor $R_4$ to ground for purposes of providing drift compensation, while a 100 K feed-back resistor $R_5$ is provided for the amplifier. This resistor is connected between the input and output of the amplifier $U_1$, at terminals 18 and 20, respectively, for imposing gain control in a manner well understood by those familiar with such devices. The output terminal 20 is connected to the input terminal 12 for the further processing circuit through a 50 K resistor $R_6$ which functions as a summing resistor.

OPERATION

It is believed that in view of the foregoing description, the operation of the device will readily be understood and it will be briefly reviewed at this point.

At this juncture, it is to be understood that the capacitor $C_1$ and resistor $R_2$ causes the terminal 16 to follow the average voltage value of the output of the transducer PT. Thus a representative of the average voltage of the transducer is voltage provided at the input of the amplifier $U_1$, and that the output of the amplifier is summed, comprising an algebraic negative of the output of the transducer, with the output of the pulse transducer PT at terminal 12. Hence, in effect, the circuit 14 monitors the average dc level of the output of the pulse transducer PT and generates a canceling signal which added to the output of the pulse transducer PT at the terminal 12 for subtracting the dc and near dc artifact signal components from the sensor output signal leaving the heart signal for further processing. Thus the relatively high voltage levels of the artifact signal components are substantially eliminated leaving the heart signal substantially unmasked for further processing.

In view of the foregoing, it is believed to be readily apparent that the attenuator circuit of the instant invention provides a practical solution to the problem of differentiating heart signals obtained from a living body through the use of a transducer of the type aforementioned, from accompanying noise signals or artifact signal components resulting from a reflection of light from the skin of the body, employing economic circuitry particularly adapted to facilitate packaging of the transducer in packages of wristwatch-size and configurations.

What is claimed is:

1. In combination with a photoelectric transducer having an output terminal connected with an input terminal for a further signal processing circuit, and adapted to be worn on the arm of a human body for providing an output signal at a variable voltage value including a heart signal component resulting from reflection of light by blood vessels present in the arm and an artifact signal component resulting from reflection of light by the skin of the arm, an artifact signal component attenuator circuit for subtracting the artifact signal component from the output signal of the transducer, comprising:
  A. a signal pick-off terminal connected to the output terminal of the transducer;
  B. signal integrating means connected to said pick-off terminal for integrating the output signal of the transducer as the output signal is applied to the pick-off terminal, comprising first resistance means connected between the pick-off terminal and the output terminal of said transducer, and capacitance means having one side connected to ground and one side connected to the pick-off terminal, whereby an integrated output signal is applied to said pick-off terminal at a voltage value comprising an average value for the voltage of the transducer output signal;
  C. an operational amplifier having an input connected to the pick-off terminal for providing an amplifier output signal comprising an algebraic negative of the integrated output signal; and
  D. means for summing the voltage value of the transducer output signal with the amplifier output signal for thus unmasking the heart signal, including second resistance means connected in series between the output terminal of the transducer and the input terminal for the further signal processing circuit, and means connecting the output of the amplifier with the input terminal for the further signal processing circuit.

* * * * *